United States Patent
Lu

(10) Patent No.: US 6,604,000 B2
(45) Date of Patent: Aug. 5, 2003

(54) METHOD AND DEVICE FOR RESPONDING TO THE DETECTION OF ISCHEMIA IN CARDIAC TISSUE

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 285 days.

(21) Appl. No.: 09/732,996

(22) Filed: Dec. 8, 2000

(65) Prior Publication Data

US 2002/0072777 A1 Jun. 13, 2002

(51) Int. Cl.$^7$ ............................................. A61N 1/365
(52) U.S. Cl. ........................................ 607/17; 600/513
(58) Field of Search .................... 607/17, 18, 23, 607/11; 600/513, 515, 519

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,809,697 A | 3/1989 | Causey, III et al. | 128/419 |
| 4,940,052 A | 7/1990 | Mann et al. | 128/419 |
| 4,944,298 A | 7/1990 | Sholder | 128/419 |
| 4,944,299 A | 7/1990 | Silvian | 128/903 |
| 5,199,428 A | 4/1993 | Obel et al. | 128/419 |
| 5,466,254 A | 11/1995 | Helland | 607/123 |
| 5,531,768 A | 7/1996 | Alferness | 607/6 |
| 5,573,550 A | 11/1996 | Zadeh et al. | 607/28 |
| 5,685,315 A | 11/1997 | McClure et al. | 128/708 |
| 6,016,443 A | 1/2000 | Ekwall et al. | 600/519 |
| 6,021,350 A | 2/2000 | Mathson | 607/17 |
| 6,128,526 A | 10/2000 | Stadler et al. | 600/517 |
| 6,233,486 B1 | 5/2001 | Ekwall et al. | 607/17 |
| 6,256,538 B1 | 7/2001 | Ekwall | 607/17 |
| 6,264,606 B1 * | 7/2001 | Ekwall et al. | 600/300 |
| 6,381,493 B1 * | 4/2002 | Stadler et al. | 607/9 |

FOREIGN PATENT DOCUMENTS

| | | | |
|---|---|---|---|
| WO | PCT/SE98/0043 | 1/1997 | A61N/1/365 |
| WO | WO98/31421 | 7/1998 | 5/42 |

OTHER PUBLICATIONS

Dilaveris, Polychronis E. et al; "Effects of Ischemia on P Wave Dispersion and Maximum P Wave Duration During Spontaneous Anginal Episodes"; PACE; vol. 22; pp. 1640–1647 (Nov. 99).

* cited by examiner

Primary Examiner—Jeffrey R. Jastrzab

(57) ABSTRACT

An apparatus and method for monitoring the patient's heart for the presence of ischemia and altering the treatment delivered by an implantable cardiac stimulation device to minimize adverse ischemic effects, e.g., angina pectoris. Embodiments of the present invention are particularly beneficial when used with a rate responsive cardiac stimulation device. Typically, a rate responsive cardiac stimulation device increases its pacing rate (up to a maximum sensor rate) in response to increases in the patient's activity level. The rate of this change is referred to in this patent as the aggressiveness of the rate responsiveness. However, in an ischemic state, the aggressiveness of the rate responsiveness may cause the heart to pace at a rate that exacerbates the ischemic effects. Accordingly, embodiments of the present invention alter the pacing regimen in one or more of the following ways. First, the maximum sensor rate is adaptively decremented in response to a detected ischemic state. Second, the aggressiveness of the rate responsiveness is adaptively decreased in response to a detected ischemic state. Third, the atrio-ventricular delay (AV) delay is adaptively extended in response to a detected ischemic state. Conversely, when an ischemic state is no longer detected, the adapted variable is incrementally returned toward its original value. Accordingly, ischemia can be minimized while still maintaining the rate responsive features of the implantable cardiac stimulation device.

25 Claims, 8 Drawing Sheets

METHOD AND DEVICE FOR RESPONDING TO THE DETECTION OF ISCHEMIA IN CARDIAC TISSUE

FIELD OF THE INVENTION

The present invention is generally directed to an implantable cardiac stimulation device and is particularly directed to a method for altering the treatment of a patient's heart in response to the detection of ischemia in the patient's cardiac tissue.

BACKGROUND OF THE INVENTION

Ischemia is a condition resulting from insufficient blood flow through the heart muscle. The reason therefore is blocking or passage congestion of coronary blood vessels of the heart. Blood penetration of the heart muscle is possible only in the diastolic phase, that is the phase between two consecutive contractions of the heart, when the aortic valve is closed. About 60% of the oxygen content inside the heart tissue is consumed during a heart contraction and in order to maintain the pumping efficiency of the heart, the consumed oxygen must be refilled until the next contraction.

An increased heart rate results in only minor shortening of the systolic phase, that is the contraction phase of the heart, and consequently an increased heart rate results mainly in a shortening of the diastolic phase, the period during which oxygen is supplied to the heart as mentioned above. An increased workload will consequently worsen the situation for an ischemic patient.

A large portion of cardiac ischemia is silent. It has been suggested that up to 80% of ischemic heart diseases are silent, i.e., a state of ischemia which the patient is not aware of. In other cases, a symptomatic (episodic) ischemia, that is angina pectoris, heart insufficiency or infarct, will force the patient, because of the associated pain, to stillness, with a reduced heart rate as a consequence.

Some patients experience a condition referred to as chronotropic incompetence in which their natural pacemaker, the sinoatrial (SA) node, is incapable of automatically adjusting the heart's pacing rate in response to increased metabolic demands, e.g., exercise. To accommodate this condition, rate modulated pacing systems have been developed which monitor the patient's activity level using an activity or physiologic sensor, e.g., an accelerometer, minute ventilation sensor or the like, to adjust the pacing rate in response to the detected activity level. In such rate modulated pacing systems, a programmable value sets the highest pacing rate that can be achieved in response to the sensor input, the so-called maximum sensor rate (MSR). When this rate modulation capability is provided to a patient experiencing ischemia, the sensor can often drive the pacing rate to a rate which exacerbates the current ischemia and may further damage the patient's heart.

It has also been proposed to provide heart stimulators provided with an ischemia detector to lower the actual stimulation rate to a base level (or below) in response to the detection of an ischemic episode, in order to slow down or stop the further development of the ischemia (see Swedish Patent Application SE 9700182-0, filed Jan. 23, 1997, or corresponding PCT application PCT/SE98/0043, filed Jan. 13, 1998).

In a dual-chamber sensing and tracking pacing system, the ventricle is stimulated in response to detected atrial activity, normally a programmable value sets the highest allowable ventricular pacing rate, the so-called maximum tracking rate (MTR). In some cases, the maximum sensor rate and the maximum tracking rate may be set so high that in an ischemic situation a prolonged high pacing rate can stimulate the heart to an infarct.

U.S. Pat. No. 6,021,350 has partially addressed this issue by reducing the MSR/MTR to a prescribed lower rate, e.g., 100–120 beats per minute (bpm), in response to a detected ischemia but at the cost of limiting the rate responsive capability of the heart stimulation device.

The present invention is directed to further improvements of the therapies delivered in response to a detected ischemia that avoid the adverse effects of ischemia while preserving the advantages of rate modulated pacing.

SUMMARY OF THE INVENTION

The present invention is directed to an apparatus and method for monitoring the patient's heart for the presence of ischemia and altering the treatment delivered by an implantable cardiac stimulation device to minimize adverse ischemic effects, e.g., angina pectoris. Embodiments of the present invention are particularly beneficial when used with a rate responsive cardiac stimulation device. Typically, a rate responsive cardiac stimulation device increases its pacing rate (up to a maximum sensor rate) in response to increases in the patient's activity level. The rate of this change is referred to in this patent as the aggressiveness of the rate responsiveness. However, in an ischemic state, the aggressiveness of the rate responsiveness may cause the heart to pace at a rate that exacerbates the ischemic effects. Accordingly, embodiments of the present invention alter the pacing regimen in one or more of the following ways. First, the maximum sensor rate is adaptively decremented in response to a detected ischemic state. Second, the aggressiveness of the rate responsiveness is adaptively decreased in response to a detected ischemic state. Third, the atrioventricular delay (AV) delay is adaptively extended in response to a detected ischemic state. Conversely, when an ischemic state is no longer detected, the adapted variable is incrementally returned toward its original value. Accordingly, ischemia can be minimized while still maintaining the rate responsive features of the implantable cardiac stimulation device.

A preferred implantable cardiac stimulation device operates according to a set of prescribed adaptable pacing parameters including a pacing rate set as a function of the patient's activity level up to a maximum sensor rate and an aggressiveness value specifying the rate of increase of the pacing rate per the increase in the patient's activity level, wherein each of the parameters has an original value in the absence of ischemia. A preferred device monitors for the presence of ischemia in the patient's heart and, once detected, incrementally alters at least one of the prescribed pacing parameters of the cardiac stimulation device by a specified amount from its respective original value.

In a further aspect of a preferred invention, the device continues to monitor for the presence of ischemia and continues to periodically incrementally alter at least one of the prescribed pacing parameters by the defined amount while ischemia is still detected. However, after a prescribed time period if the ischemia is absent, the device incrementally adjusts the altered pacing parameter back towards its original value.

In a still further aspect of a preferred invention, the prescribed adaptable pacing parameters are only altered within a defined range of increments.

Preferred embodiments include the maximum sensor rate (MSR), the aggressiveness and the AV/PV delay values within the set of prescribed adaptable pacing parameters. When ischemia is present, one or more of the following may occur: the MSR is decreased, the aggressiveness is decreased, and the AV/PV delay values are increased. Conversely, after a prescribed time period without ischemia, one or more of the following may occur: the MSR is increased, the aggressiveness is increased, and the AV/PV delay values are decreased.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention provides an improved apparatus and method for treating ischemia with an implantable cardiac stimulation device, e.g., a pacemaker or an implantable cardioverter/defibrillator (ICD).

Figure 1:
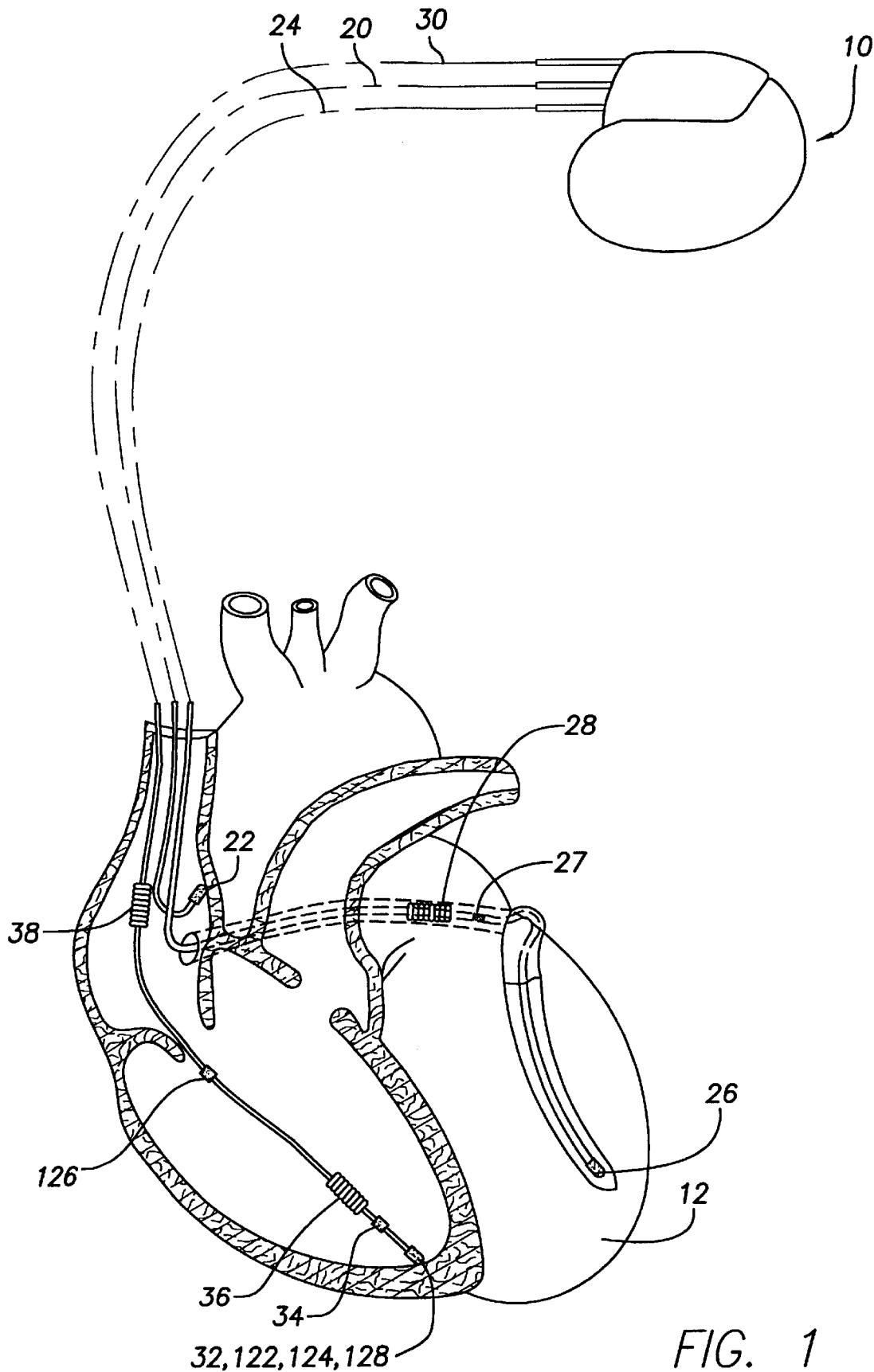
FIG. 1 is a simplified diagram illustrating an implantable cardiac stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive left atrial and left ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
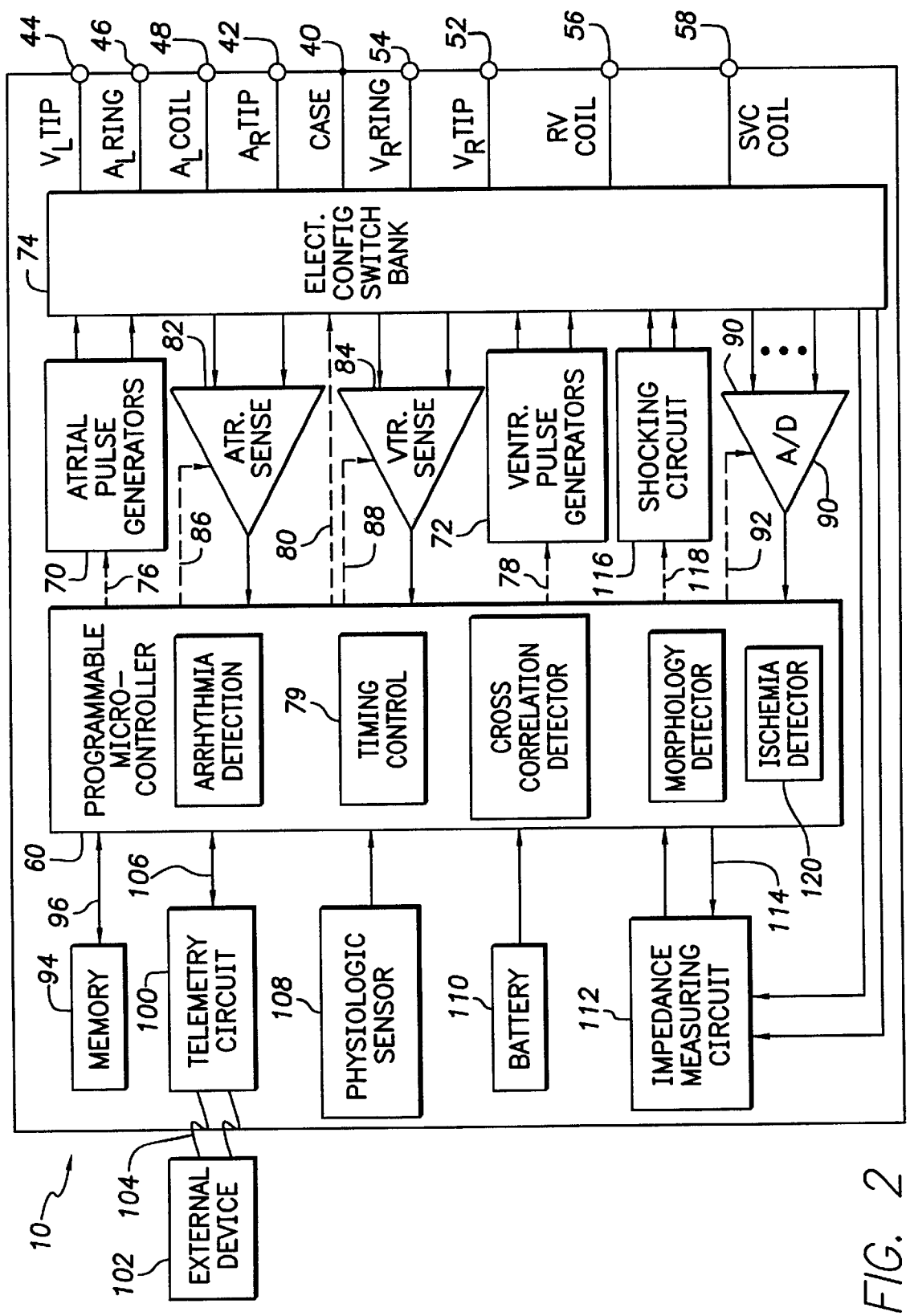
FIG. 2 is a functional block diagram of an exemplary rate responsive implantable cardiac stimulation device illustrating the basic elements of a stimulation device which can provide cardioversion, defibrillation and pacing stimulation in multiple chambers of the heart and configured to adapt its pacing regimen in response to a detected ischemic state.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the right atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry or processor, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.) and the state-machines of U.S. Pat. No. 4,712,555 (Sholder) and U.S. Pat. No. 4,944,298 (Sholder). For a more detailed description of the various timing intervals used within the stimulation device and their inter-relationships, see U.S. Pat. No. 4,788,980 (Mann et al.). The '052, '555, '298 and '980 patents are incorporated herein by reference.

As shown in FIG. 2, atrial pulse generators 70 and ventricular pulse generators 72 generate pacing stimulation pulses for delivery by the right atrial lead 20, the right ventricular lead 30, and/or the coronary sinus lead 24 via an electrical configuration switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each of the sensing circuits, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 may enable capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating (pacing) parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.), which patents are hereby incorporated herein by reference.

In the preferred embodiment, the stimulation device 10 further includes a physiologic sensor 108, commonly referred to as a "rate responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) which the atrial and ventricular pulse generators, 70 and 72, use to generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of physiologic sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further include magnet detection circuitry (not shown) coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch bank 74 so that any desired electrode may be used. The type of impedance measuring circuit is not critical to the present invention and is shown only for completeness.

In a rate responsive pacemaker, the pacing rate is adjusted as a function of the sensed activity rate up to a maximum sensor rate (MSR). Generally, the pacing rate increases linearly with increases in the sensed activity level. This responsiveness of the pacing rate to changes in the activity level is referred to in this invention as the aggressiveness of the activity sensor response. Typically, this relationship and the rate response aggressiveness can be shown graphically such that it exhibits a slope or average slope essentially corresponding to a factor:

(pacing rate)/(sensor rate)

which generally reflects the rate response aggressiveness. Generally, this aggressiveness is programmable via the external device 102. However, in a preferred embodiment of the present invention, the aggressiveness is additionally adjusted according to the presence of ischemia. As discussed further below, the rate response aggressiveness is preferably reduced when ischemia is detected.

In the case where the stimulation device 10 is intended to operate as an implantable cardioverter/defibrillator (ICD) device, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (10–40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 0.5–40 joules), delivered asynchronously (since R-waves or P-waves may be too disorganized) and pertaining exclusively to the treatment of fibrillation. Accordingly, the microcontroller 60 is capable of controlling the synchronous or asynchronous delivery of the shocking pulses.

Embodiments of the present invention additional include an ischemia detector 120. Various types of ischemia detectors have been described in the prior art. See, for example, U.S. Pat. Nos. 5,199,428; 5,531,768; 6,016,443; 6,021,350; and 6,128,526; each of which is incorporated herein by reference in their entirety. The present invention is primarily directed toward the response of a rate modulated pacing system to the detection of ischemia and is not dependent on the particular implementation of an ischemia detector. As shown in the aforementioned patents, various implementations of ischemia detectors are known, some of which use additional sensors while others process signals that are already present in the aforedescribed device, e.g., intracardiac electrograms. For completeness, the following describes some of these exemplary implementations of ischemia detectors.

It is well known that ischemia conditions can be detected by analysis of a surface ECG (see, for example, Dilaveris, P. E., et al., Effects of Ischemia on P Wave Dispersion and Maximum P Wave Duration during Spontaneous Anginal Episodes. PACE 1999; 22:1640–1647). Furthermore, the "surface" ECGs may be synthesized from the intracardiac electrograms by the ischemia detector portion 120 of the microcontroller 60 to perform a similar analysis. Due to the preferred multi-site environment, e.g., using electrodes 22, 26, 27, 28, 32, 34, 36, 38, shown in FIG. 1, the intracardiac electrograms sensed via the data acquisition system 90 may represent many different vectors and may further enhance the capability of detecting the presence of ischemia.

It is also known that the heart wall becomes thicker and stiffer as a result of an ischemic state. Thus, an ischemic state may be detected by studying changes in the moving pattern of the heart wall. Accordingly, a lead bend sensor 122 may be located at the distal end portion of lead 30. This lead bend sensor 122 may be formed of a material which generates an electric signal when subjected to bending movements, e.g., a piezoelectric material, the signal being supplied to the ischemia detector 120 via lead 30.

An ischemia state may also be detected by AC impedance measurements in the ventricle since this impedance is related to the blood filling of the ventricle. For this purpose, the impedance measuring circuit 112 may be used to detect impedance measurement variations from the electrodes and supply these signals to the ischemia detector 120. Further, an ischemic state may be detected from the sound absorption in the heart tissue since this absorption changes with changes in the stiffness of the heart tissue. Thus, one microphone 124 may be mounted at the distal end of the lead 30 and another microphone 126 may be mounted on the lead 30 such that it will be positioned in the upper part of the right ventricle after implantation of the lead 30, see FIG. 1. In this way it is possible to measure the absorption of sound waves generated at the upper part of the right ventricle by valve closure during propagation through the right ventricle down to the microphone 124 situated at the ventricular bottom. The signals picked up by the microphones 124, 126 are fed to the ischemia detector 120 for analysis.

An ischemia state may also be detected by evaluating blood pressures and cardiac outputs as well since an ischemia will affect the efficiency of the pumping of the heart. Thus, an ischemic state may be determined by measuring the difference between the systolic and the diastolic pressures and comparing this difference from one heartbeat to the difference obtained from the next heartbeat. An ischemic state may also be detected by monitoring the systolic pressure over time. For these pressure measurements, a pressure sensor 126 in FIG. 1 is used. The pressure signals obtained from the pressure sensor 128 is supplied through the lead 30 to the ischemia detector 120.

An ischemic state may also be detected by evaluating the cardiac output. For this purpose, a flow sensor (not shown) may be positioned, e.g., in the pulmonary artery, for measuring the cardiac output.

An ischemic state may also be detected by evaluating the patient workload and the patient breathing activity. The workload can be sensed by the physiologic sensor 108 and the breathing activity can be determined by measuring the AC impedance between two of the electrodes 22, 26, 27, 28, 32, 34, 36, 38, or between one of the electrodes 22, 26, 27, 28, 32, 34, 36, 38, and the case 40 of the stimulation device 10. An ischemic state is then detected from the occurrence of a predetermined relation between sensed workload and sensed breathing activity.

Another way of detecting an ischemic state is to monitor sensed repolarization of the heart and patient workload. Information about repolarization of the heart may be obtained from intracardiac electrograms via the data acquisition system 90 and the patient workload may be monitored via the physiologic sensor 108. An ischemic state is then detected from the occurrence of a predetermined relation between sensed repolarization and sensed workload, i.e., the physiologic state.

Figure 3A:
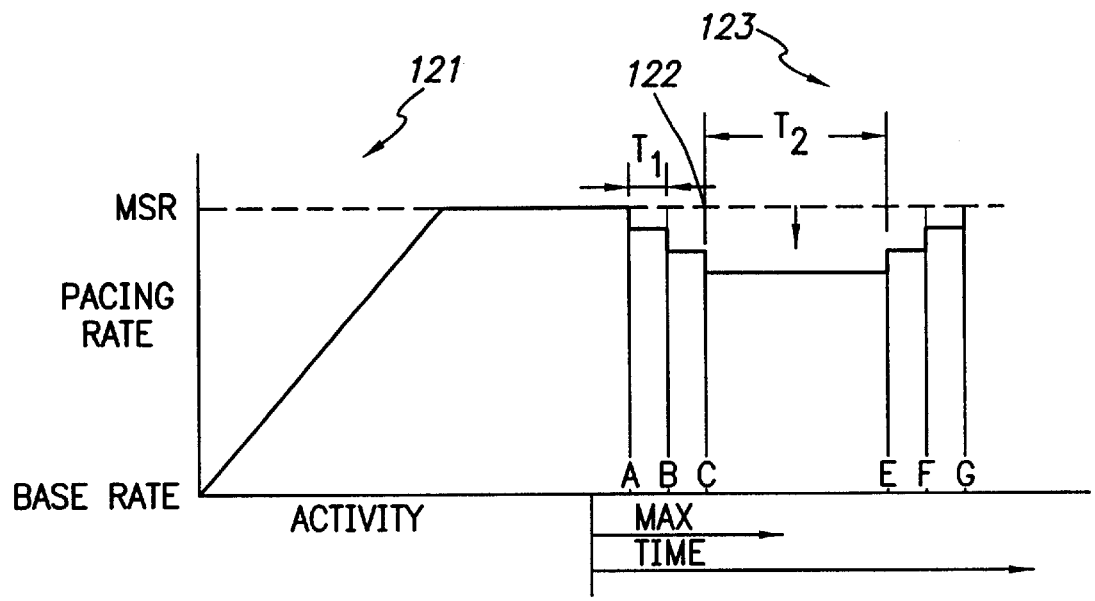
FIG. 3A shows a simplified diagram of an exemplary relationship between the demand pacing rate and the sensed activity level in its first portion 121. In the second portion 123 of FIG. 3A, the sensed activity level is presumed to be steady at a rate corresponding to the maximum sensor rate (MSR) and ischemia is detected. Accordingly, the MSR is adaptively adjusted to attempt to eliminate the ischemia.

FIG. 3A shows a graph that essentially corresponds to the relationship between the patient's activity level, as measured by the physiologic sensor 108, and the demand pacing rate currently used by the stimulation device 10, i.e., the rate at which the stimulation device 10 will stimulate the patient's heart in the absence of intrinsic cardiac activity. Typically, this relationship is essentially linear but other relationships are also possible. However, in all cases, the aggressiveness of the rate responsiveness may be reflected by the slope of this graph, e.g., at one point or an average of multiple points, and the patient's demand pacing rate will increase as the patient's sensed activity level increases. However, the base rate increase per activity level increase will reflect the present aggressiveness. The demand pacing rate is not permitted to increase indefinitely and is limited by a predetermined value, the maximum sensor rate (MSR).

The first portion 121 of FIG. 3A can be viewed as displaying the aforementioned relationship between the demand pacing rate and the activity level. The second portion 123 of FIG. 3A shows an exemplary response of the present invention if the activity level remains at or above its maximum level and an ischemic state is detected by the ischemia detector 120. If an ischemic state were not detected, the MSR (and thus the demand pacing rate) would remain at its maximum value, designated by dashed line 122 and determined by the aggressiveness of the stimulation device 10 to the present activity level. However, at this pacing level, the ischemia will persist and may progress, even causing painful symptoms, e.g., angina pectoris. Accordingly, in a first variation, embodiments of the present invention adaptively adjust the MSR in response to the absence or presence of ischemia. An exemplary adjustment is as follows:

$$\text{Adjusted } MSR = MSR - (X_1 * \Delta_{MSR})$$

where MSR is the originally programmed MSR value, $X_1$ is adaptively adjusted between 0 and $m_1$, e.g., 6, and $\Delta_{MSR}$ is a predetermined rate decrement, e.g., 10 bpm.

Preferably, $X_1$ is increased each time that an ischemic state is determined/reconfirmed according to a first sample time period $T_1$, e.g., 0.5 to 3 seconds, and decremented when an ischemic state is not detected for a second sample time period $T_2$, e.g., 1–5 minutes. As previously stated, this adaptive adjustment of $X_1$ occurs within the predetermined range of between 0 and $m_1$.

Figure 4:
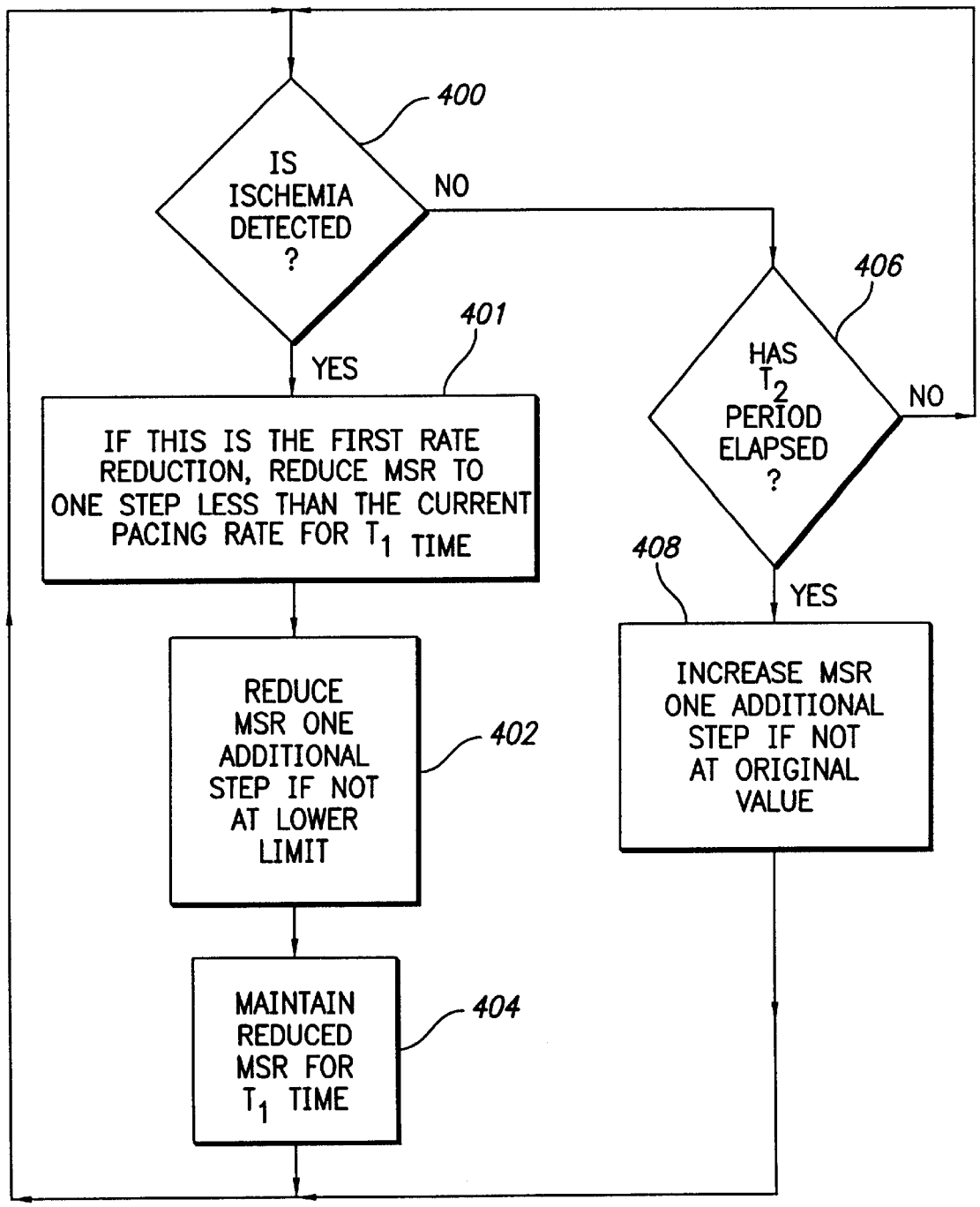
FIG. 4 shows a simplified exemplary flow chart of a process that adaptively adjusts the MSR to attempt to eliminate the ischemia as shown in FIG. 3A.

This adaptive process can be best seen by referencing the second portion 123 of FIG. 3A in conjunction with the exemplary flow chart of FIG. 4 (see blocks 400–408). FIG. 3A presumes that the measured activity level has been maintained at a level that corresponds to the MSR. Should the ischemia result in angina pectoris, it is most probable that the patient would have already reduced his activity level and, accordingly, the demand pacing rate would have already decreased. However, in the case of a "silent" ischemia, an asymptomatic condition, the patient may remain at the present activity level which is facilitating the ischemia. At block 400, the ischemia detector 120 periodically checks for the presence of ischemia. At time A, ischemia is first detected and the adjusted MSR is set to one $\Delta_{MSR}$, e.g., 10 ppm, less than the current pacing rate in block 401 at the onset of the ischemia. Additionally, this adjusted MSR is maintained for a time period $T_1$. In the example of FIG. 3A, the ischemia first occurs at the MSR. At time B, the adjusted MSR is reduced in block 402 by one $\Delta_{MSR}$ increment, e.g., 10 bpm, and retained in block 404 at that level for a prescribed time period $T_1$. (Alternatively, this function may be accomplished by increasing $X_1$, within its prescribed limit. While this mathematical implementation may be easier to comprehend, additions and subtractions may reduce the computational demands on the microcontroller 60. Either implementation is equivalent for the purpose of the present invention.) Again, it is determined in block 400 that ischemia is still present. Accordingly, the adjusted MSR is again decremented in block 402 (block 401 is skipped on subsequent iterations), this time at time C. This process can continue until the pacing rate is at a lower limit, e.g., 60 ppm, or when the ischemia is no longer detected. Accordingly, the next time that block 400 is executed, the process is directed to block 406. Until a second prescribed time period $T_2$ has elapsed, block 406 will continuously direct the process back to block 400 to see if the ischemia is still absent. Finally, at time E, the ischemia will have been absent for a time period $T_2$ and the adjusted MSR is incremented back towards its original MSR value, e.g., by decrementing $X_1$. This process is shown repeating at times F and G. The adjusted MSR has returned to its original MSR state at time G.

Figure 3B:
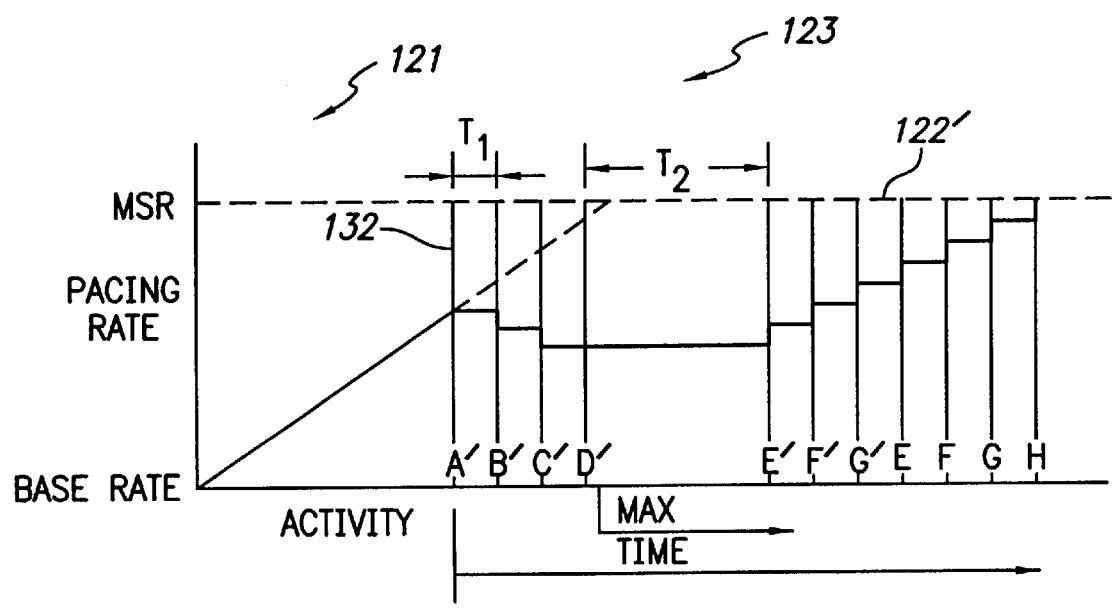
FIG. 3B shows a simplified diagram of an exemplary relationship between the demand pacing rate and the sensed activity level in its first portion 121. In the second portion 123 of FIG. 3B, the sensed activity level is presumed to be increasing and ischemia is detected while the pacing rate is below the MSR. Accordingly, the pacing rate is adaptively adjusted downward to attempt to eliminate the ischemia.

FIG. 3B shows an example in which the onset of ischemia occurs below the MSR. Accordingly at time A', the adjusted MSR is initially reduced in block 401 from the MSR to one $\Delta_{MSR}$, e.g., 10 ppm, less than the current pacing rate (see reduction line 132). Subsequent reductions occur in block 402 until ischemia is no longer detected. At time E', time period $T_2$ has elapsed (according to block 406) and in block 408, the adjusted MSR is increased. In this example, the adjusted MSR increases each $T_1$ time period until the adjusted MSR returns to the original MSR value. Furthermore, the pacing rate can also increase to the MSR if the exemplary activity level is high enough to require pacing at the MSR (in the absence of ischemia).

Figure 3C:
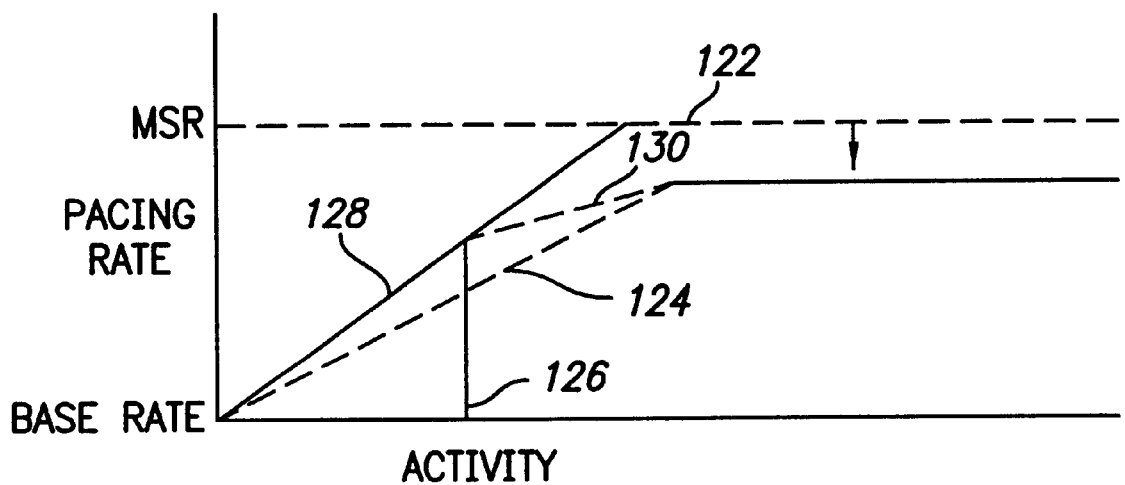
FIG. 3C shows a simplified diagram of an exemplary relationship between the demand pacing rate and the sensed activity level that demonstrates a next technique at eliminating ischemia by adaptively adjusting the aggressiveness of the rate responsiveness of the stimulation device, e.g., the slope, and the MSR.
Figure 5:
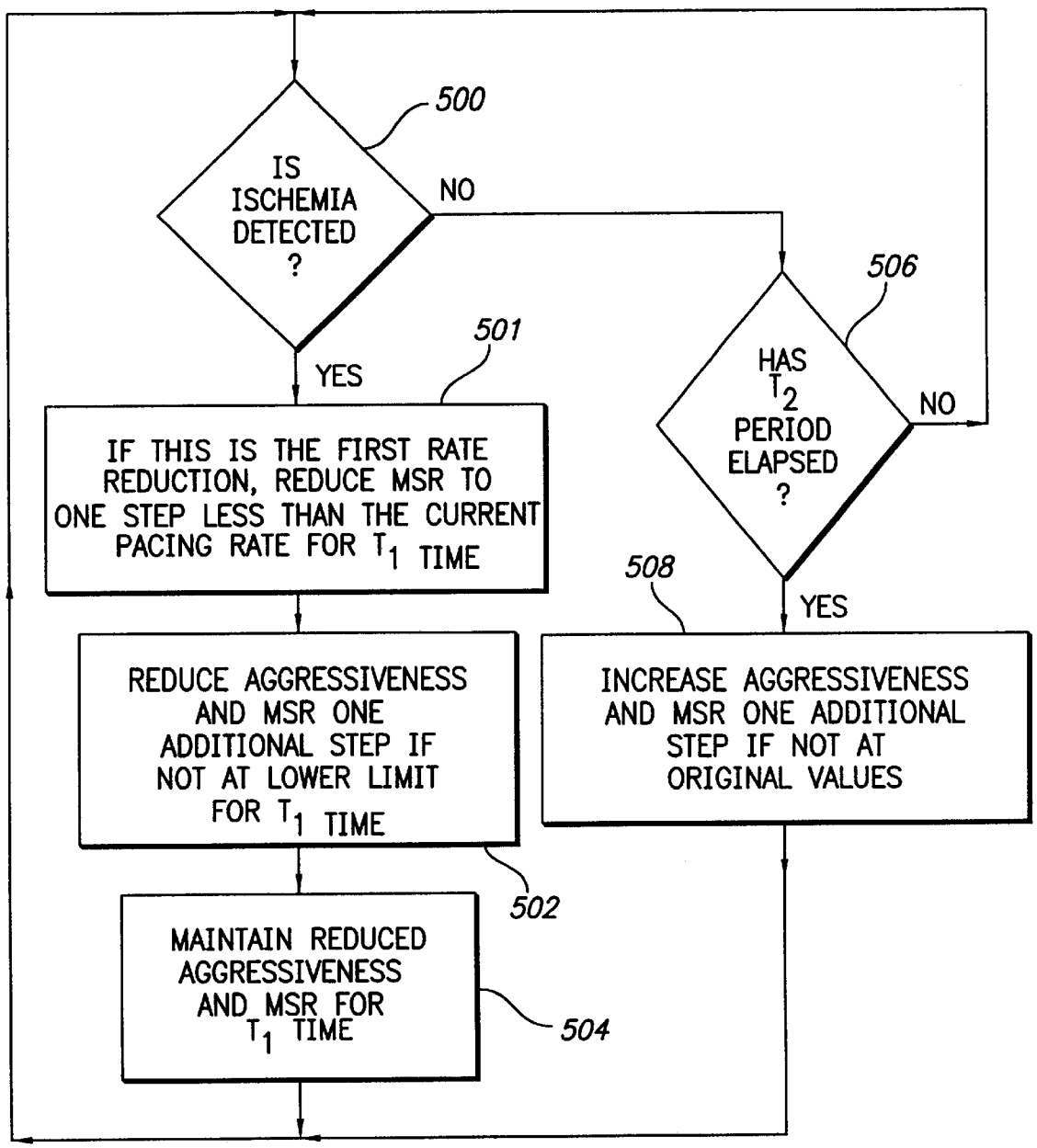
FIG. 5 shows a simplified exemplary flow chart of a process that adaptively adjusts the MSR and the aggressiveness of the rate responsiveness of the stimulation device to attempt to eliminate the ischemia as shown in FIG. 3C.

FIG. 3C also displays the aforementioned relationship between the demand pacing rate and the activity level. However, in this figure, ischemia is treated via a two step process. First, as previously described in relation to FIG. 3A and FIG. 4, the MSR is adapted downward to avoid the pacing rates that have facilitated the onset of ischemia. Additionally, in this embodiment, the aggressiveness of the rate responsiveness of the stimulation device 10 is also decreased, i.e., the slope of the relationship between the demand pacing rate and the sensed activity is decreased, as seen in reduced slope 124. Alternatively, the aggressiveness may be decreased in multiple stages since it is more likely that pacing at a high pacing rate will trigger the onset of ischemia than pacing at a low pacing rate. For example, the present relationship may be maintained until a prescribed activity level, e.g., level 126, and the slope may be reduced afterwards to decrease the likelihood of triggering ischemia at higher pacing rates, resulting in a relationship graphically displayed by graph portions 128, 130. Similarly, this relationship may be further divided into a plurality of ranges. FIG. 5 shows an exemplary flow chart, similar to that previously described in FIG. 4, renumbered with a 5XX number series that are analogous to those previously described in the 4XX number series and generally operates in a similar manner. However, to reflect the differences of this embodiment, blocks 502, 504 and 508 have been modified. Accordingly, the description below is primarily directed to these differences.

In block 502 (in response to the detection of ischemia in block 500), the aggressiveness of the rate responsiveness is decreased (as discussed above) and the MSR is incrementally adjusted (as discussed in relation to FIG. 3A). Once the ischemia is no longer detected in block 500 for a period of time (as determined in block 506), the aggressiveness and the MSR are incrementally adjusted back toward their original values in block 508. While this exemplary flow chart shows both the aggressiveness and the MSR decreasing during each iteration, other variations are also considered to be within the scope of the present invention. For example, the MSR may be adjusted during one or more iterations and, if ischemia is still present, the process will continue with one or more iterations where only the aggressiveness is altered.

Figure 6:
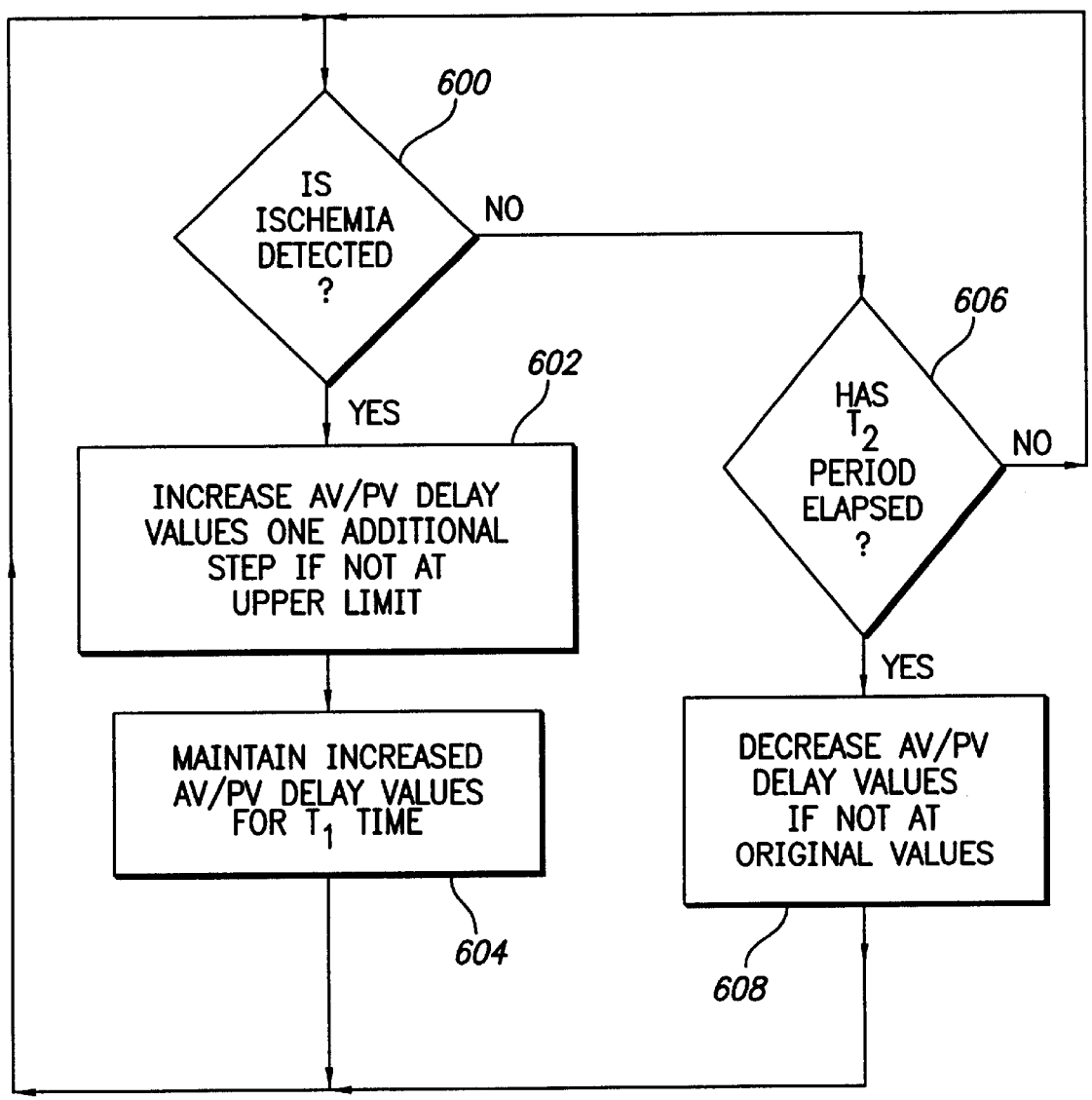
FIG. 6 shows a simplified exemplary flow chart of a process that adaptively adjusts the AV/PV delays to attempt to eliminate the detected ischemia.

Ischemia may also result from the ventricle having insufficient time for filling as controlled by the programmed AV/PV delay. Accordingly, if the AV/PV delays are extended the additional filling timing may eliminate, minimize or at least avoid the ischemia from presenting angina pectoris. FIG. 6 shows an exemplary algorithm for treating ischemia by adaptively altering the AV/PV delays. FIG. 6 is similar to that previously described in FIG. 4, renumbered with a 6XX number series that are analogous to those previously described in the 4XX number series and generally operates in a similar manner. However, to reflect the differences of this embodiment, blocks 602, 604 and 608 have been modified. Accordingly, the description below is primarily directed to these differences.

In block 602 (in response to the detection of ischemia in block 600), the AV/PV delays are incrementally increased (as discussed above). Once the ischemia is no longer detected in block 600 for a period of time (as determined in block 606), the AV/PV delays are incrementally adjusted back toward their original values in block 608.

Figure 7:
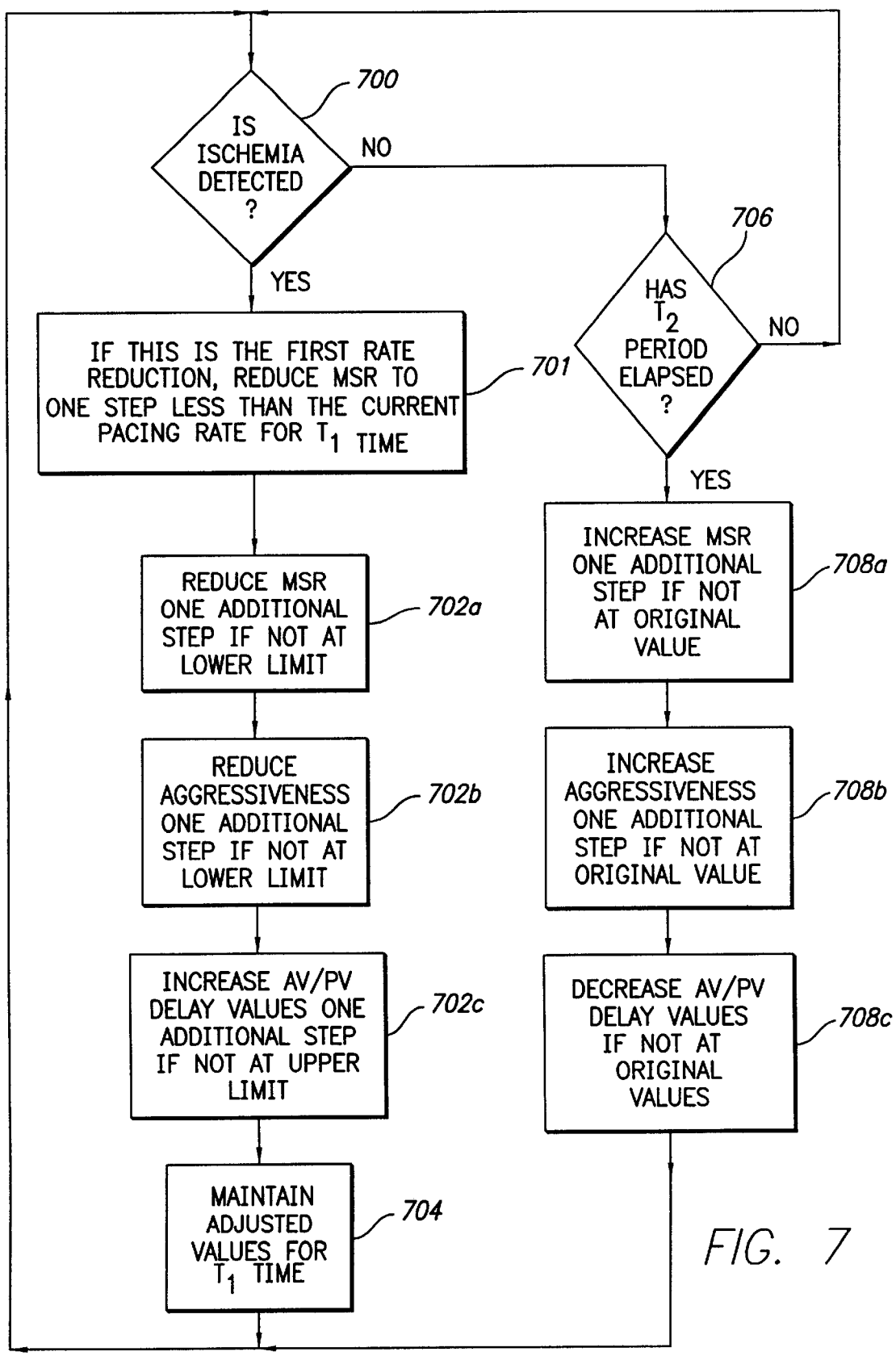
FIG. 7 shows a simplified exemplary flow chart of a process that attempts to eliminate ischemia by adaptively adjusting, the MSR and aggressiveness of the rate responsiveness (as described in relation to FIG. 5) as well as adaptively adjusting the AV/PV delays (as described in relation to FIG. 6).

FIG. 7 shows a simplified exemplary flow chart of a process that attempts to eliminate ischemia by adaptively adjusting the MSR and aggressiveness of the rate responsiveness (as described in relation to FIG. 5) as well as adaptively adjusting the AV/PV delays (as described in relation to FIG. 6). FIG. 7 is similar to that previously described in FIG. 4, renumbered with a 7XX number series that are analogous to those previously described in the 4XX number series and generally operates in a similar manner. However, to reflect the differences of this embodiment, blocks 702*a–c* (replacing block 402), 704, and 708*a–c* (replacing block 408) have been modified. Accordingly, the description below is primarily directed to these differences.

In block 702*a* (in response to the detection of ischemia in block 700), the adjusted MSR is incrementally reduced (as discussed above). In block 702*b*, the aggressiveness of the rate responsiveness is decreased (as discussed above). In block 702*c*, the AV/PV delays are incrementally increased (as discussed above). Once the ischemia is no longer detected in block 700 for a period of time (as determined in block 706), each of the adjusted values is incrementally adjusted back toward their original values in blocks 708*a*–708*c*. FIG. 7 has shown an exemplary case where the MSR, aggressiveness, and the AV/PV delays are adjusted during each iteration (702*a*–702*c*) as long as ischemia is detected (subject to their limit values). However, in alternative implementations adjustments to these values may be interleaved during each consecutive $T_1$ time period. For example, the MSR may be adjusted downward for one or more iterations, followed by reductions in the aggressiveness for one or more iterations, followed by increases in the AV/PV delay for one or more iterations. Additionally, the recovery phase of the algorithm (708*a*–708*c*) may use an analogous or alternate variation of that corresponding to 702*a*–702*c*. One of ordinary skill in the art can envision a wide range of variations of this algorithm.

Accordingly, what has been shown is a method and device for treating ischemia with an implantable cardiac stimulation device. While the invention has been described by means of specific embodiments and applications thereof, it is understood that numerous modifications and variations could be made thereto by those skilled in the art without departing from the spirit and scope of the invention. For example, various combinations of parameters have been shown being adjusted in response to the detection of ischemia. However, one of ordinary skill in the art would recognize that these exemplary algorithms could be modified to adjust different combinations of variables at different rates or times or variable rates and times. All such variations are considered to be within the scope of the present invention. Additionally, while the present invention is of particular use when it is used with a rate responsive cardiac stimulation device, the capability to adaptively adjust pacing parameters, e.g., AV or PV delays, in response to ischemia can also be beneficially used with a non rate responsive cardiac stimulation device. It is therefore to be understood that within the scope of the claims, the invention may be practiced otherwise than as specifically described herein.

What is claimed is:

1. A method of treating ischemia of a patient's heart using an implantable cardiac stimulation device operating according to a set of prescribed adaptable pacing parameters including a pacing rate set as a function of the patient's activity level up to a maximum sensor rate and an aggressiveness value specifying the rate of increase of the pacing rate per the increase in the patient's activity level, wherein each of the parameters has an original value in the absence of ischemia, the method comprising the steps of:

detecting the presence of ischemia in the patient's heart; and incrementally altering at least one of the prescribed adaptable pacing parameters of the cardiac stimulation device by a specified amount, initially from its respective original value, in response to detecting the presence of ischemia in the patient's heat, and continuing to periodically incrementally alter at least one of the prescribed adaptable pacing parameters by the specified amount while ischemia is still detected, and incrementally altering the at least one of the prescribed adaptable pacing parameters back toward its original value in response to not detecting the presence of ischemia by the ischemia detecting means for a prescribed period of time.

2. The method of claim 1 wherein the step of periodically incrementally altering at least one of the prescribed adaptable pacing parameters is only performed within a defined range of increments.

3. A method of treating ischemia of a patient's heart using an implantable cardiac stimulation device operating according to a set of prescribed adaptable pacing parameters including a pacing rate set as a function of the patient's activity level up to a maximum sensor rate and an aggressiveness value specifying the rate of increase of the pacing rate per the increase in the patient's activity level, wherein each of the parameters has an original value in the absence of ischemia, the method comprising the steps of:

detecting the presence of ischemia in the patient's heart: and incrementally decreasing the rate response aggressiveness of the cardiac stimulation device by a specified amount, initially from its respective original value, in response to detecting the presence of ischemia in the patient's heart.

4. The method of claim 3 wherein the rate of increase of the pacing rate per the increase in the patient's activity level is defined in at least two activity level ranges and decreasing the rate response aggressiveness value in response to the presence of ischemia specifies decreasing the rate of increase in at least one of the defined activity level ranges.

5. The method of claim 3 wherein the step of incrementally altering at least one of the prescribed adaptable pacing parameters comprises incrementally decreasing the maximum sensor rate and incrementally decreasing the rate response aggressiveness.

6. A method of treating ischemia of patient's heart using an implantable cardiac stimulation device operating according to a set of prescribed adaptable pacing parameters including a pacing rate set as a function of the patient's activity level up to a maximum sensor rate and an aggressiveness value specifying the rate of increase of the pacing rate per the increase in the patient's activity level, wherein each of the parameters has an original value in the absence of ischemia, the method comprising the steps of:

detecting the presence of ischemia in the patient's heart;

incrementally altering at least one of the prescribed adaptable pacing parameters of the cardiac stimulation device by a specified amount, initially from its respective original value, in response to detecting the presence of ischemia in the patient's heart; and incrementally altering at least one of the prescribed adaptable pacing parameters of the cardiac stimulation device back toward its original value in response to not detecting the presence of ischemia in the patient's heart for a prescribed time period.

7. A method of treating ischemia of a patient's heart using an implantable cardiac stimulation device operating according to a set of prescribed adaptable pacing parameters including a pacing rate set as a function of the patient's activity level up to a maximum sensor rate and an aggressiveness value specifying the rate of increase of the pacing rate per the increase in the patient's activity level, wherein each of the parameters has an original value in the absence of ischemia, the method comprising the steps of:

detecting the presence of ischemia in the patient's heart;

incrementally altering at least one of the prescribed adaptable pacing parameters of the cardiac stimulation device by a specified amount, initially from its respective original value, in response to detecting the presence of ischemia in the patient's heart;

wherein the prescribed adaptable pacing parameters additionally include AV/PV delay values defining the delay between an atrial event and delivery of a ventricular stimulation pulse by the cardiac stimulation device and the incrementally altering step comprises increasing the AV/PV delay values by a specified amount in response to detecting the presence of ischemia in the patient's heart.

8. The method of claim 7 additionally comprising the step of incrementally decreasing the AV/PV delay values by a specified amount in response to not detecting the presence of ischemia in the patient's heart for a prescribed period of time.

9. The method of claim 7 wherein the step of incrementally altering at least one of the prescribed adaptable pacing parameters comprises incrementally decreasing the maximum sensor rate, incrementally decreasing the rate response aggressiveness, and incrementally increasing the AV/PV delay values.

10. An implantable cardiac stimulation device configured for stimulating a patient's heart through at least one electrode implanted in electrical contact with selected cardiac tissue, the cardiac stimulation device comprising:

at least one pulse generator configured for electrical coupling to the at least one electrode and configured to generate stimulation pulses at a pacing rate according to a set of prescribed adaptable pacing parameters, wherein each parameter has an original value in the absence of ischemia;

an ischemia detector configured for determining the presence of ischemia in at least a portion of the cardiac tissue;

a controller, coupled to the ischemia detector for periodically altering at least one of the prescribed adaptable pacing parameters of the cardiac stimulation device by a specified incremental amount, initially from its respective original value, in response to detecting the presence of ischemia by the ischemia detector; wherein the controller additionally alters at least one of the prescribed adaptable pacing parameters of the cardiac stimulation device in response to the ischemia detector not detecting the presence of ischemia for a prescribed period.

11. An implantable cardiac stimulation device configured for stimulating a patient's heart through at least one electrode implanted in electrical contact with selected cardiac tissue, the cardiac stimulation device comprising:

at least one pulse generator configured for electrical coupling to the at least one electrode and configured to generate stimulation pulses at a pacing rate according to a set of prescribed adaptable pacing parameters, wherein each parameter has an original value in the absence of ischemia;

an ischemia detector configured for determining the presence of ischemia in at least a portion of the cardiac tissue;

a controller, coupled to the ischemia detector for periodically altering at least one of the prescribed adaptable pacing parameters of the cardiac stimulation device by a specified incremental amount, initially from its respective original value, in response to detecting the presence of ischemia by the ischemia detector;

wherein the at least one electrode includes an electrode in electrical contact with an atrium of the patient's heart and an electrode in electrical contact with a ventricle of the patient's heart and the at least one pulse generator includes an atrial pulse generator and a ventricular pulse generator to respectively generate atrial and ventricular stimulation pulses to the atrium and ventricle of the patient's heart; and wherein the prescribed adaptable pacing parameters include an AV delay defining the delay between delivery of an atrial stimulation pulse and delivery of a ventricular stimulation pulse by the cardiac stimulation device and the controller increases the AV delay by a prescribed amount in response to the ischemia detector detecting the presence of ischemia.

12. The cardiac stimulation device of claim 11 wherein the controller decreases the increased AV delay in response to the ischemia detector not detecting the presence of ischemia for a prescribed period of time.

13. An implantable cardiac stimulation device configured for stimulating a patient's heart through at least one electrode implanted in electrical contact with selected cardiac tissue, the cardiac stimulation device comprising:

at least one pulse generator configured for electrical coupling to the at least one electrode and configured to generate stimulation pulses at a pacing rate according to a set of prescribed adaptable pacing parameters, wherein each parameter has an original value in the absence of ischemia;

an ischemia detector configured for determining the presence of ischemia in at least a portion of the cardiac tissue;

a controller, coupled to the ischemia detector for periodically altering at least one of the prescribed adaptable pacing parameters of the cardiac stimulation device by a specified incremental amount, initially from its respective original value, in response to detecting the presence of ischemia by the ischemia detector;

wherein the at least one electrode includes an electrode in electrical contact with an atrium of the patient's heart and an electrode in electrical contact with a ventricle of the patient's heart and the at least one pulse generator is configured to deliver ventricular stimulation pulses to the ventricle of the patient's heart, the cardiac stimulation device additional comprising:

a sensing circuit configured to receive a signal from the electrode in electrical contact with the atrium of the patient's heart for detecting intrinsic P-waves from the patient's heart; and wherein the pacing parameters additionally include a PV delay defining the delay between a sensed P-wave and delivery of a ventricular stimulation pulse by the cardiac stimulation device and the controller increases the PV delay by a specified amount in response to the ischemia detector detecting the presence of ischemia.

14. The cardiac stimulation device of claim 13 wherein the controller decreases the increased PV delay in response to the ischemia detector not detecting the presence of ischemia for a prescribed period of time.

15. An implantable cardiac stimulation device configured for stimulating a patient's heart through at least one electrode implanted in electrical contact with selected cardiac tissue, the cardiac stimulation device comprising:

at least one pulse generator configured for electrical coupling to the at least one electrode and configured to generate stimulation pulses at a pacing rate according to a set of prescribed adaptable pacing parameters, wherein each parameter has an original value in the absence of ischemia;

an ischemia detector configured for determining the presence of ischemia in at least a portion of the cardiac tissue;

a controller, coupled to the ischemia detector for periodically altering at least one of the prescribed adaptable pacing parameters of the cardiac stimulation device by a specified incremental amount, initially from its respective original value, in response to detecting the presence of ischemia by the ischemia detector;

wherein the controller continues to periodically incrementally alter at least one of the prescribed adaptable pacing parameters by the specified amount while ischemia is still detected by the ischemia detector and wherein the controller is operative to incrementally alter the at least one of the prescribed adaptable pacing parameters back toward its original value in response to not detecting the presence of ischemia by the ischemia detector for a prescribed period of time.

16. The cardiac stimulation device of claim 15 wherein the controller incrementally alters at least one of the prescribed adaptable pacing parameters only within a defined range of increments.

17. An implantable cardiac stimulation device configured for stimulating a patient's heart through at least one electrode implanted in electrical contact with selected cardiac tissue, the cardiac stimulation device comprising:

at least one pulse generator configured for electrical coupling to the at least one electrode and configured to generate stimulation pulses at a pacing rate according to a set of prescribed adaptable pacing parameters, wherein each parameter has an original value in the absence of ischemia;

an ischemia detector configured for determining the presence of ischemia in at least a portion of the cardiac tissue;

a controller, coupled to the ischemia detector for periodically altering at least one of the prescribed adaptable pacing parameters of the cardiac stimulation device by a specified incremental amount, initially from its respective original value, in response to detecting the presence of ischemia by the ischemia detector;

an activity sensor for determining the patients activity level;

a controller, coupled to the pulse generator and the activity sensor for determining the pacing rate as a function of the determined patient's activity level up to a maximum sensor rate and according to a rate response aggressiveness value specifying the rate of increase of the pacing rate per the increase in the patient's activity level, wherein the prescribed adaptable pacing parameters include the maximum sensor rate and the rate response aggressiveness values; and wherein the controller is configured to incrementally alter at least one of the prescribed adaptable pacing parameters of the cardiac stimulation device by a specified amount from its respective original value in response to detecting the presence of ischemia by the ischemia detector;

wherein the controller incrementally decreases the rate response aggressiveness in response to ischemia being detected by the ischemia detector.

18. The cardiac stimulation device of claim 17 wherein the rate of increase of the pacing rate per the increase in the patient's activity level is defined in at least two activity level ranges and the controller decreases the rate response aggressiveness in response to ischemia being detected by the ischemia detector by decreasing the rate of increase in at least one of the defined activity level ranges.

19. The cardiac stimulation device of claim 17 wherein the controller incrementally decreases the maximum sensor rate and incrementally decreases the rate response aggressiveness in response to ischemia being detected by the ischemia detector.

20. The cardiac stimulation device of claim 17 wherein the controller incrementally alters at least one of the prescribed adaptable pacing parameters of the cardiac stimulation device back toward its original value in response to not detecting the presence of ischemia by the ischemia detector for a prescribed time period.

21. The cardiac stimulation device of claim 17 wherein the prescribed adaptable pacing parameters additionally include AV/PV delay values defining the delay between an atrial event and delivery of a ventricular stimulation pulse by the cardiac stimulation device and the controller incrementally increases the AV/PV delay values by a specified amount in response to detecting the presence of ischemia by the ischemia detector.

22. The cardiac stimulation device of claim 21 wherein the controller incrementally decreases the AV/PV delay values by a specified amount in response to not detecting the presence of ischemia by the ischemia detector for a prescribed period of time.

23. The cardiac stimulation device of claim 17 wherein the controller incrementally decreases the maximum sensor rate, incrementally decreases the rate response aggressiveness, and incrementally increases the AV/PV delay values in response to detecting the presence of ischemia by the ischemia detector.

24. An implantable cardiac stimulation device configured for stimulating a patients heart through at least one electrode implanted in electrical contact with selected cardiac tissue, the cardiac stimulation device comprising:

means for generating and delivering stimulation pulses to the at least one electrode according to a set of prescribed adaptable pacing parameters, wherein each pacing parameter has an original value in the absence of ischemia;

means for detecting the presence of ischemia in at least a portion of the cardiac tissue; and means for periodically altering at least one of the prescribed adaptable pacing parameters of the cardiac stimulation device by a specified incremental amount, from its respective original value, in response to detecting the presence of ischemia by the ischemia detecting means wherein at least one of the prescribed adaptable pacing parameters is incrementally altered to minimize the presence of ischemia in response to detecting the presence of ischemia by the ischemia detecting means;

wherein the altered pacing parameter is incrementally altered back toward its original value in response to not detecting the presence of ischemia by the ischemia detecting means for a prescribed period of time.

25. A method of treating ischemia of a patient's heart using an implantable cardiac stimulation device operating according to a set of one or more prescribed adaptable pacing parameters including at least a pacing rate set as a function of the patient's activity level up to a maximum sensor rate, wherein each of the parameters has an original value in the absence of ischemia, the method comprising the steps of:

detecting the presence of ischemia in the patient's heart;

determining the pacing rate when ischemia is detected;

altering the maximum sensor rate according to the pacing rate when ischemia is detected;

incrementally altering at least one of the prescribed adaptable pacing parameters of the cardiac stimulation device by a specified amount in response to continuing to detect the presence of ischemia in the patient's heart.

* * * * *